US012773557B2

(12) United States Patent
Steinke et al.

(10) Patent No.: US 12,773,557 B2
(45) Date of Patent: Oct. 27, 2026

(54) ENHANCED SYSTEM AND METHOD FOR EVOKED POTENTIAL CLASSIFICATION

(71) Applicant: Boston Scientific Neuromodulation Corporation, Valencia, CA (US)

(72) Inventors: G. Karl Steinke, Valencia, CA (US); Tomasz Mark Fraczek, Yucaipa, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 168 days.

(21) Appl. No.: 18/766,156

(22) Filed: Jul. 8, 2024

(65) Prior Publication Data

US 2025/0018194 A1 Jan. 16, 2025

Related U.S. Application Data

(60) Provisional application No. 63/525,750, filed on Jul. 10, 2023.

(51) Int. Cl.
*A61B 5/388* (2021.01)
*A61N 1/05* (2006.01)
(Continued)

(52) U.S. Cl.
CPC ....... *A61N 1/36135* (2013.01); *A61N 1/0534* (2013.01); *A61N 1/36157* (2013.01);
(Continued)

(58) Field of Classification Search
CPC .............. A61N 1/36135; A61N 1/0534; A61N 1/36157; A61N 1/37247; A61N 1/3756;
(Continued)

(56) References Cited

U.S. PATENT DOCUMENTS 10,130,813 B2 * 11/2018 Crowder ............ A61N 1/36139
12,070,603 B2 8/2024 Steinke et al.
(Continued)

FOREIGN PATENT DOCUMENTS

WO WO-2025014875 A1 1/2025

OTHER PUBLICATIONS

"International Application Serial No. PCT/US2024/037056, International Preliminary Report on Patentability mailed Jan. 22, 2026", 12 pgs.

(Continued)

*Primary Examiner* — Carl H Layno
*Assistant Examiner* — Owen Lewis Marsh
(74) *Attorney, Agent, or Firm* — Schwegman Lundberg & Woessner, P.A.

(57) ABSTRACT

This document discusses a computer-implemented method of operating a neurostimulation device to deliver electrical neurostimulation when connected to an implantable stimulation lead. The method includes delivering neurostimulation to a subject using the neurostimulation device; recording electrical signals sensed using the implantable stimulation lead; extracting one or more features from the recorded electrical signals; detecting clustering of the one or more extracted features of the recorded electrical signals; and identifying, by the neurostimulation device, an evoked response signal of interest from among the recorded electrical signals using the detected clustering of the one or more extracted features of the recorded electrical signals.

19 Claims, 13 Drawing Sheets

(51) Int. Cl.
*A61N 1/36* (2006.01)
*A61N 1/372* (2006.01)
*A61N 1/375* (2006.01)
*A61N 1/378* (2006.01)

(52) U.S. Cl.
CPC ....... *A61N 1/37247* (2013.01); *A61N 1/3756* (2013.01); *A61N 1/3787* (2013.01)

(58) Field of Classification Search
CPC .............. A61N 1/3787; A61N 1/36062; A61N 1/36064; A61N 1/36067; A61N 1/36082; A61N 1/36139; A61B 5/388; A61B 5/395; A61B 5/4058; A61B 5/7221; A61B 5/7264
See application file for complete search history.

(56) References Cited

U.S. PATENT DOCUMENTS

| | | | | |
|---|---|---|---|---|
| 2009/0163973 | A1 | 6/2009 | Meyer et al. | |
| 2012/0016445 | A1* | 1/2012 | Zhu | A61N 1/36185 607/59 |
| 2016/0228705 | A1 | 8/2016 | Crowder et al. | |
| 2018/0078210 | A1 | 3/2018 | Snow et al. | |
| 2021/0342641 | A1* | 11/2021 | Bhattacharya | G06N 20/10 |
| 2022/0305270 | A1 | 9/2022 | Esteller | |
| 2023/0023842 | A1 | 1/2023 | Steinke et al. | |
| 2023/0166111 | A1* | 6/2023 | Hageman | A61B 5/383 607/59 |

OTHER PUBLICATIONS

"International Application Serial No. PCT/US2024/037056, International Search Report mailed Oct. 25, 2024", 5 pgs.
"International Application Serial No. PCT/US2024/037056, Written Opinion mailed Oct. 25, 2024", 9 pgs.
Gao, Caroline, et al., "An overview of clustering methods with guidelines for application in mental health research", Psychiatry Research, Elsevier Ireland Ltd, IE, vol. 327, (May 27, 2023).
Ghaderi, Parviz, et al., "Kernel Density Estimation of Electromyographic Signals and Ensemble Learning for Highly Accurate Classification of a Large Set of Hand/Wrist Motions", Frontiers In Neuroscience, vol. 16, (Mar. 9, 2022).
Sheikhpour, Razieh, et al., "A kernelized non-parametric classifier based on feature ranking in anisotropic Gaussian kernel", ARXIV, vol. 267, 545-555.
T., Jones Andrew, et al., "logKDE: log-transformed kernel density estimation", Journal Of Open Source Software, vol. 3, No. 28, (Aug. 6, 2018), 870 pgs.
Tran, et al., "KNN-kernel density-based clustering for high-dimensional multivariate data", Computational Statistics And Data Analysis, North-Holland, Amsterdam, NL, vol. 51, No. 2, (Oct. 29, 2006), 513-525.
Vivien, Gaillet, et al., "A machine-learning algorithm correctly classifies cortical evoked potentials from both visual stimulation and electrical stimulation of the optic nerve", Journal Of Neural Engineering, Institute Of Physics Publishing, Bristol, GB, vol. 18, No. 4, (Apr. 26, 2021), 46031 pgs.
Zhiguo, Zhang, "Identification of Detailed Time-Frequency Components in Somatosensory Evoked Potentials", IEEE Transactions On Neural Systems And Rehabilitation Engineering, IEEE, USA, vol. 17, No. 3, (Jun. 1, 2010), 245-254.

* cited by examiner

ENHANCED SYSTEM AND METHOD FOR EVOKED POTENTIAL CLASSIFICATION

CLAIM OF PRIORITY

This application claims the benefit of U.S. Provisional Application No. 63/525,750 filed on Jul. 10, 2023, which is hereby incorporated by reference in its entirety.

TECHNICAL FIELD

This document relates generally to medical devices and more particularly to a system for neurostimulation.

BACKGROUND

Neurostimulation, also referred to as neuromodulation, has been proposed as a therapy for a number of conditions. Examples of neurostimulation include Spinal Cord Stimulation (SCS), Deep Brain Stimulation (DBS), Peripheral Nerve Stimulation (PNS), and Functional Electrical Stimulation (FES). Implantable neurostimulation systems have been applied to deliver such a therapy. An implantable neurostimulation system may include an implantable neurostimulator, also referred to as an implantable pulse generator (IPG), and one or more implantable leads each including one or more electrodes. The implantable neurostimulator delivers neurostimulation energy through one or more electrodes placed on or near a target site in the nervous system. An external programming device can be used to program the implantable neurostimulator with stimulation parameters controlling the delivery of the neurostimulation energy.

In one example, the neurostimulation energy is delivered in the form of electrical neurostimulation pulses. The delivery is controlled using stimulation parameters that specify spatial (where to stimulate), temporal (when to stimulate), and informational (patterns of pulses directing the nervous system to respond as desired) aspects of a pattern of neurostimulation pulses. Neurostimulation systems may offer many programmable options for the parameters of the neurostimulation to customize the neurostimulation therapy for a specific patient. For some types of neurostimulation (e.g., DBS) the efficacy of the neurostimulation for the patient may depend on an intricate balance of stimulation location coupled with the programmed stimulation waveform. Finding the right stimulation location can be a complicated and time consuming process. The process is compounded by the ability to correctly distinguish evoked response signals from noise. Basing decisions regarding neurostimulation therapy using signals that are actually noise can lead to patient dissatisfaction with the neurostimulation.

SUMMARY

Electrical neurostimulation energy can be delivered in the form of electrical neurostimulation pulses to treat a neurological condition of the patient. The pulses can be delivered using an implantable stimulation lead. The lead can have multiple electrodes and may be configurable into many electrode configurations. Neurostimulation can be provided to the patient and electrical signals evoked by the neurostimulation can be sensed and analyzed to customize the neurostimulation to a particular patient. However, the recording can include useful and non-useful information.

Example 1 includes subject matter (such as a method of operating a neurostimulation device when the device is connected to an implantable stimulation lead) comprising delivering neurostimulation to a subject using the neurostimulation device, recording electrical signals sensed using the implantable stimulation lead, extracting one or more features from the recorded electrical signals, detecting clustering of the one or more extracted features of the recorded electrical signals, and identifying an evoked response signal of interest from among the recorded electrical signals using the detected clustering of the one or more extracted features of the recorded electrical signals.

In Example 2, the subject matter of Example 1 optionally includes measuring a magnitude of the recorded electrical signals and a time of a greatest magnitude value of the recorded electrical signals, detecting a cluster of recorded electrical signals in a feature space including the greatest magnitude values and the times of the greatest magnitude values of the recorded electrical signals, and selecting the evoked response signal of interest from the detected cluster.

In Example 3, the subject matter of one or both of Examples 1 and 2 optionally includes classifying the recorded electrical signals as either evoked response signals or artifact signals using kernel density estimation (KDE) of the one or more extracted features of the recorded electrical signals.

In Example 4, the subject matter of Example 3 optionally includes determining a value of a kernel function for the recorded electrical signals using the one or more extracted features of the recorded electrical signals, determining the KDE for the kernel function values, identifying a higher density set of recorded electrical signals included in a region of the KDE having a density greater than a threshold density, and classifying a recorded electrical signal as the evoked response signal of interest when the recorded electrical signal is included in the higher density set of recorded electrical signals.

In Example 5, the subject matter of one or both of Examples 3 and 4 optionally includes calculating a normalized log of the KDE, and identifying the higher density set of recorded electrical signals as the electrical signals included in a region of the normalized log of the KDE having a density greater than the threshold density.

In Example 6, the subject matter of one or any combination of Examples 3-5 optionally includes determining a value of a kernel function for the recorded electrical signals using the one or more extracted features of the recorded electrical signals, determining the KDE for the kernel function values, identifying a low density set of recorded electrical signals included in a region of the KDE having a density less than a threshold density, and classifying a candidate recorded electrical signal as an artifact signal when the candidate recorded electrical signal is included in the low density set of recorded electrical signals.

In Example 7, the subject matter of one or any combination of Examples 1-2 optionally includes determining correlation of the one or more extracted features among the recorded electrical signals.

In Example 8, the subject matter of one or any combination of Examples 1-2 optionally includes computing a distance between the recorded electrical signals in a feature space derived for the recorded electrical signals.

In Example 9, the subject matter of one or any combination of Examples 1-8 optionally includes the neurostimulation device adjusting the neurostimulation to the subject using the one or more extracted features of the identified evoked response signal of interest.

Example 10 includes subject matter (such as a neurostimulation device) or can optionally be combined with one or nay combination of Examples 1-9 to include such subject matter, comprising a stimulation circuit configured to deliver electrical neurostimulation to a subject when coupled to an implantable stimulation lead, a sensing circuit configured to sense electrical signals when coupled to the stimulation lead, a control circuit operatively coupled to the stimulation circuit and the sensing circuit, and signal processing circuitry. The control circuit is configured to initiate delivery of neurostimulation to the subject and record sensed electrical signals resulting from the neurostimulation. The signal processing circuitry is configured to extract one or more features from the recorded electrical signals, detect clustering of the one or more extracted features of the recorded electrical signals, and classify a recorded electrical signal as an evoked response signal of interest according to the detected clustering of the one or more extracted features of the recorded electrical signals.

In Example 11, the subject matter of Example 10 optionally includes signal processing circuitry configured to identify a group of the recorded electrical signals as evoked response signals using kernel density estimation (KDE) of the one or more extracted features of the recorded electrical signals.

In Example 12, the subject matter of Example 11 optionally includes signal processing circuitry configured to determine a value of a kernel function for the recorded electrical signals using the one or more extracted features of the recorded electrical signals, determine the KDE for the kernel function values, identify a higher density set of recorded electrical signals included in a region of the KDE having a density greater than a threshold density, and classify the recorded electrical signal as the evoked response signal of interest when the recorded electrical signal is included in the higher density set of recorded electrical signals.

In Example 13, the subject matter of Example 12 optionally includes signal processing circuitry configured to calculate a normalized log of the KDE, and identify the higher density set of recorded electrical signals as the electrical signals included in a region of the normalized log of the KDE having a density greater than the threshold density.

In Example 14, the subject matter of one or any combination of Examples 11-13 optionally includes signal processing circuitry configured to determine a value of a kernel function for the recorded electrical signals using the one or more extracted features of the recorded electrical signals, determine the KDE for the kernel function values, identify a low density set of recorded electrical signals included in a region of the KDE having a density less than a threshold density, and classify a recorded electrical signal as an artifact signal when the candidate recorded electrical signal is included in the low density set of recorded electrical signals.

In Example 15, the subject matter of one or any combination of Examples 10-14 optionally includes signal processing circuitry configured to detect the clustering of the one or more extracted features of the recorded electrical signals using correlation of the one or more extracted features among the recorded electrical signals.

In Example 16, the subject matter of one or any combination of Examples 10-15 optionally includes signal processing circuitry configured to derive a feature space for the one or more extracted features of the recorded electrical signals, and compute distance between the recorded electrical signals in the derived feature space.

In Example 17, the subject matter of one or any combination of Examples 10-16 optionally includes signal processing circuitry configured to measure a magnitude of the recorded electrical signals and a time of the greatest magnitude value of the recorded electrical signals, determine a cluster of recorded electrical signals in a feature space including the greatest magnitude values and the times of the greatest magnitude values of the recorded electrical signals, and identify the evoked response signal of interest from the recorded electrical signals included in the determined cluster.

In Example 18, the subject matter of Example 17 optionally includes signal processing circuitry configured to identify multiple evoked response signals of interest in the identified cluster of recorded electrical signals, and a control circuit configured to set a stimulation configuration of the neurostimulation to the stimulation configuration that produced the highest amplitude evoked response signal of the identified evoked response signals of interest.

Example 19 includes subject matter (or can be combined with one or any combination of Examples 1-18 to include such subject matter) such as a computer readable storage medium including instructions that when performed by processing circuitry of a neurostimulation system, cause the neurostimulation system to perform actions including delivering neurostimulation energy to at least one implantable neurostimulation lead of the neurostimulation system, recording electrical signals sensed using the implantable stimulation lead, extracting one or more features from the recorded electrical signals, detecting clustering of the one or more extracted features of the recorded electrical signals, classifying the recorded electrical signals as either an evoked response activity signal or a signal artifact using the clustering of the one or more extracted features of the recorded electrical signals, and adjusting the neurostimulation based on the one or more extracted features of at least one identified evoked response signal.

In Example 20, the subject matter of Example 19 optionally includes instructions that when performed by processing circuitry of a neurostimulation system, cause the neurostimulation system to perform actions including determining a value of a kernel function for the recorded electrical signals using the one or more extracted features of the recorded electrical signals, determining a kernel density estimation (KDE) for the kernel function values, identifying a higher density set of the recorded electrical signals included in a region of the KDE having a density greater than a threshold density, and identifying a lower density set of the recorded electrical signals included in a region of the KDE having a density lower than the threshold density, and classifying the recorded electrical signal as the evoked response signal when the recorded electrical signal is included in the higher density set of recorded electrical signals, and classifying the recorded electrical signal as the signal artifact when the recorded electrical signal is included in the lower density set of recorded electrical signals.

These non-limiting examples can be combined in any permutation or combination. This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses devices, systems and methods for programming and delivering electrical neurostimulation to a patient or subject. Advancements in neuroscience and neurostimulation research have led to a demand for delivering complex patterns of neurostimulation energy for various types of therapies. The present system may be implemented using a combination of hardware and software designed to apply any neurostimulation (neuromodulation) therapy, including but not being limited to DBS, SCS, PNS, FES, Occipital Nerve Stimulation (ONS), Sacral Nerve Stimulation (SNS), and Vagus Nerve Stimulation (VNS) therapies.

Figure 1:
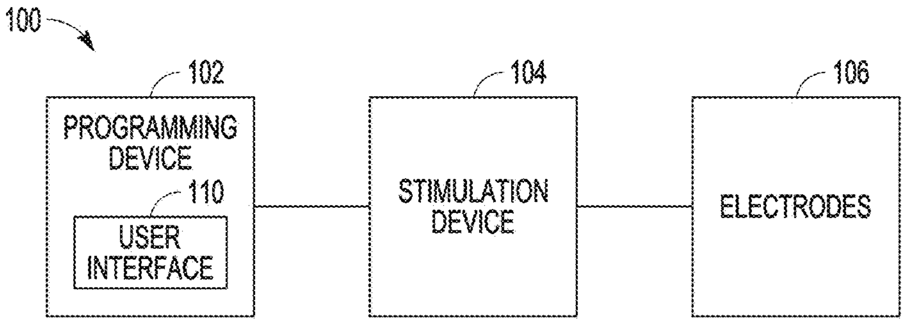
FIG. 1 is an illustration of portions of an example of a neurostimulation system.

FIG. 1 illustrates an example of portions of a neurostimulation system 100. System 100 includes electrodes 106, a stimulation device 104, and a programming device 102. Electrodes 106 are configured to be placed on or near one or more neural targets in a patient. Stimulation device 104 is configured to be electrically connected to electrodes 106 and deliver neurostimulation energy, such as in the form of electrical pulses, to the one or more neural targets though electrodes 106. The delivery of the neurostimulation is controlled by using multiple stimulation parameters, such as stimulation parameters specifying a pattern of the electrical pulses and a selection of electrodes through which each of the electrical pulses is delivered. In various embodiments, at least some of the stimulation parameters are programmable by a user, such as a physician or other caregiver who treats the patient using system 100. Programming device 102 provides the user with accessibility to the user-programmable parameters. In various embodiments, programming device 102 is configured to be communicatively coupled to stimulation device 104 via a wired or wireless link.

In this document, a "user" includes a physician or other clinician or caregiver who treats the patient using system 100; a "patient" includes a person who receives or is intended to receive neurostimulation delivered using system 100. In various embodiments, the patient can be allowed to adjust their treatment using system 100 to certain extent, such as by adjusting certain therapy parameters and entering feedback and clinical effect information.

In various embodiments, programming device 102 can include a user interface 110 that allows the user to control the operation of system 100 and monitor the performance of system 100 as well as conditions of the patient including responses to the delivery of the neurostimulation. The user can control the operation of system 100 by setting and/or adjusting values of the user-programmable parameters.

In various embodiments, user interface 110 can include a graphical user interface (GUI) that allows the user to set and/or adjust the values of the user-programmable parameters by creating and/or editing graphical representations of various stimulation waveforms. Such waveforms may include, for example, a waveform representing a pattern of neurostimulation pulses to be delivered to the patient as well as individual waveforms that are used as building blocks of the pattern of neurostimulation pulses, such as the waveform of each pulse in the pattern of neurostimulation pulses. The GUI may also allow the user to set and/or adjust stimulation fields each defined by a set of electrodes through which one or more neurostimulation pulses represented by a waveform are delivered to the patient. The stimulation fields may each be further defined by the distribution of the current of each neurostimulation pulse in the waveform. In various embodiments, neurostimulation pulses for a stimulation period (such as the duration of a therapy session) may be delivered to multiple stimulation fields.

In various embodiments, system 100 can be configured for neurostimulation applications. User interface 110 can be configured to allow the user to control the operation of system 100 for neurostimulation. For example, system 100 as well as user interface 110 can be configured for DBS applications. The DBS configurations include various features that may simplify the task of the user in programming the stimulation device 104 for delivering DBS to the patient, such as the features discussed in this document.

Figure 2:
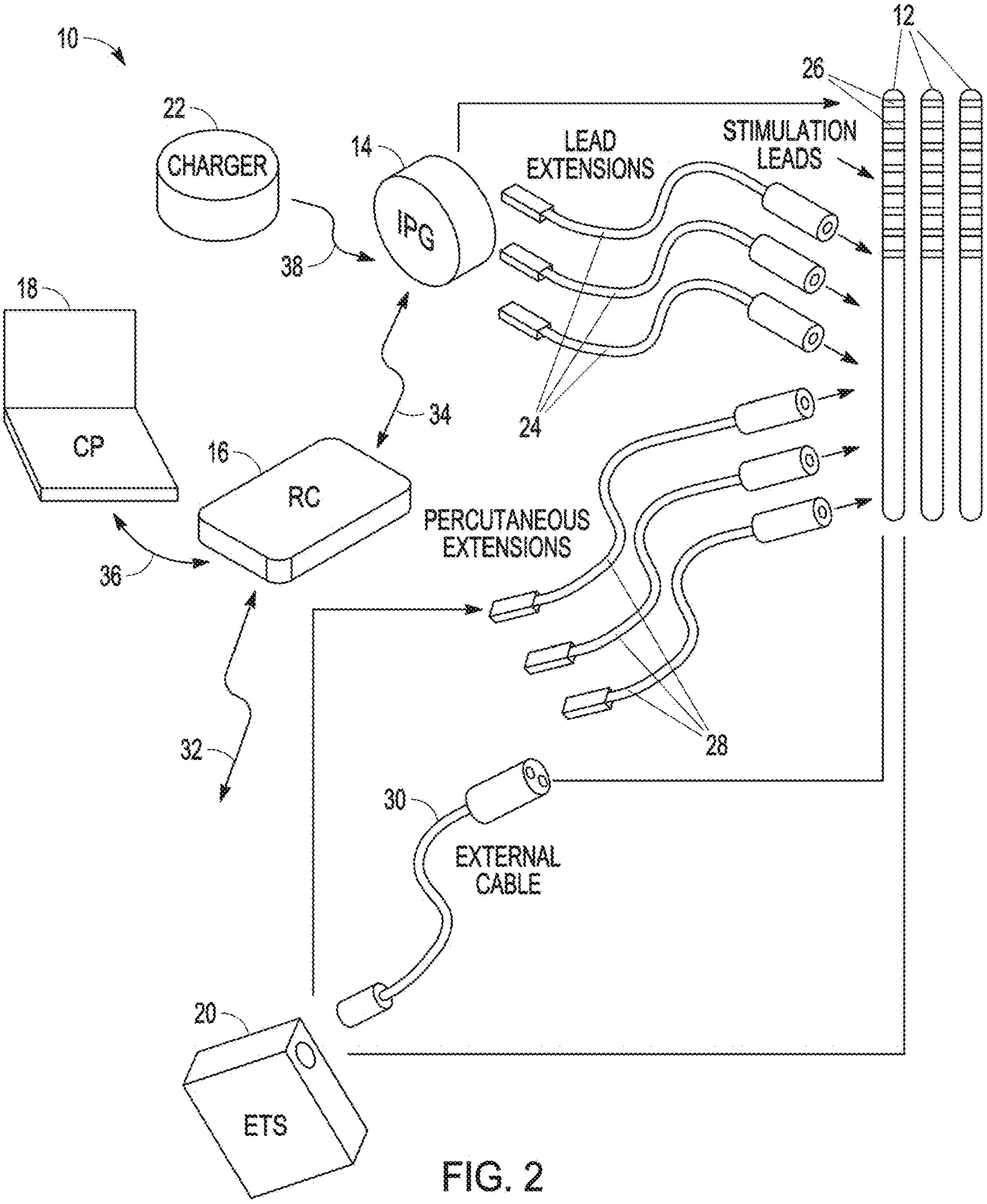
FIG. 2 is an illustration of portions of another example of a neurostimulation system.

FIG. 2 is an illustration of portions of another example of a neurostimulation system 10 that includes one or more stimulation leads 12 and an implantable pulse generator (IPG) 14. The system 10 can also include one or more of an external remote control (RC) 16, a clinician's programmer (CP) 18, an external trial stimulator (ETS) 20, or an external charger 22. The IPG 14 can optionally be physically connected via one or more lead extensions 24, to the stimulation lead(s) 12. Each lead carries multiple electrodes 26 arranged in an array. The IPG 14 includes pulse generation circuitry that delivers electrical stimulation energy in the form of, for example, a pulsed electrical waveform (i.e., a temporal series of electrical pulses) to the electrode array 26 in accordance with a set of stimulation parameters. The IPG 14 can be implanted into a patient's body, for example, below the patient's clavicle area or within the patient's buttocks or abdominal cavity. The implantable pulse generator can have multiple stimulation channels (e.g., 8 or 16) which may be independently programmable to control the magnitude of the current stimulus from each channel. The IPG 14 can have one, two, three, four, or more connector ports, for receiving the terminals of the leads 12.

The ETS 20 may also be physically connected, optionally via the percutaneous lead extensions 28 and external cable 30, to the stimulation leads 12. The ETS 20, which may have similar pulse generation circuitry as the IPG 14, can also deliver electrical stimulation energy in the form of, for example, a pulsed electrical waveform to the electrode array 26 in accordance with a set of stimulation parameters. One difference between the ETS 20 and the IPG 14 is that the ETS 20 is often a non-implantable device that is used on a trial basis after the neurostimulation leads 12 have been implanted and prior to implantation of the IPG 14, to test the responsiveness of the stimulation that is to be provided. Any functions described herein with respect to the IPG 14 can likewise be performed with respect to the ETS 20.

The RC 16 may be used to telemetrically communicate with or control the IPG 14 or ETS 20 via a wireless communications link 32. Once the IPG 14 and neurostimulation leads 12 are implanted, the RC 16 may be used to telemetrically communicate with or control the IPG 14 via communications link 34. The communication or control allows the IPG 14 to be turned on or off and to be programmed with different stimulation parameter sets. The IPG 14 may also be operated to modify the programmed stimulation parameters to actively control the characteristics of the electrical stimulation energy output by the IPG 14. The CP 18 allows a user, such as a clinician, the ability to program stimulation parameters for the IPG 14 and ETS 20 in the operating room and in follow-up sessions. The CP 18 may perform this function by indirectly communicating with the IPG 14 or ETS 20, through the RC 16, via a wireless communications link 36. Alternatively, the CP 18 may directly communicate with the IPG 14 or ETS 20 via a wireless communications link (not shown). The stimulation parameters provided by the CP 18 are also used to program the RC 16, so that the stimulation parameters can be subsequently modified by operation of the RC 16 in a stand-alone mode (i.e., without the assistance of the CP 18).

Figure 3:
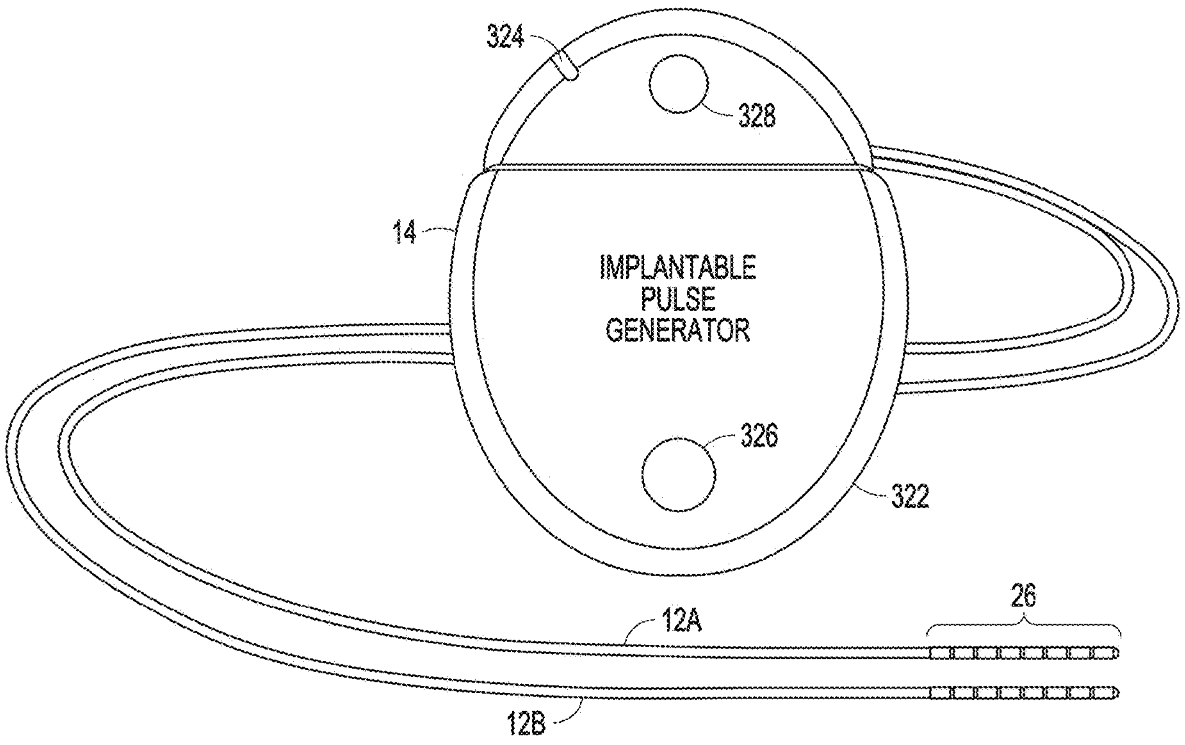
FIG. 3 is an illustration of an example of an implantable pulse generator (IPG) and an implantable lead system.

FIG. 3 is an illustration of an example of an IPG 14 (e.g., IPG 14 in FIG. 2) and an implantable lead system that includes stimulation leads (e.g., stimulation leads 12 in FIG. 2). The IPG 14 can be used as stimulation device 104 in FIG. 1. As illustrated in FIG. 3, IPG 14 that can be coupled to implantable leads 12A and 12B at a proximal end of each lead. The distal end of each lead includes electrical contacts or electrodes 26 for contacting a tissue site targeted for electrical neurostimulation. As illustrated in FIG. 3, leads 12A and 12B each include 8 electrodes 26 at the distal end. The number and arrangement of leads 12A and 12B and electrodes 26 as shown in FIGS. 2 and 3 are only examples, and other numbers and arrangements are possible. In various examples, the lead electrodes 26 are ring electrodes. In various examples the lead electrodes 26 include one or more segmented electrodes.

The IPG 14 can include a hermetically sealed IPG case 322 to house the electronic circuitry of IPG 14. IPG 14 can include an electrode 326 formed on IPG case 322. IPG 14 can include an IPG header 324 for coupling the proximal ends of leads 12A and 12B. IPG header 324 may optionally also include an electrode 328. One or both of electrodes 326 and 328 may be used as a reference electrode.

The implantable leads and electrodes may be configured by shape and size to provide electrical neurostimulation energy to a neuronal target included in the subject's brain. Neurostimulation energy can be delivered in a monopolar (also referred to as unipolar) mode using electrode 326 or electrode 328 and one or more electrodes selected from electrodes 26. Neurostimulation energy can be delivered in a bipolar mode using a pair of electrodes of the same lead (lead 12A or lead 12B). Neurostimulation energy can be delivered in an extended bipolar mode using one or more electrodes of a lead (e.g., one or more electrodes of lead 12A) and one or more electrodes of a different lead (e.g., one or more electrodes of lead 12B).

Figure 4:
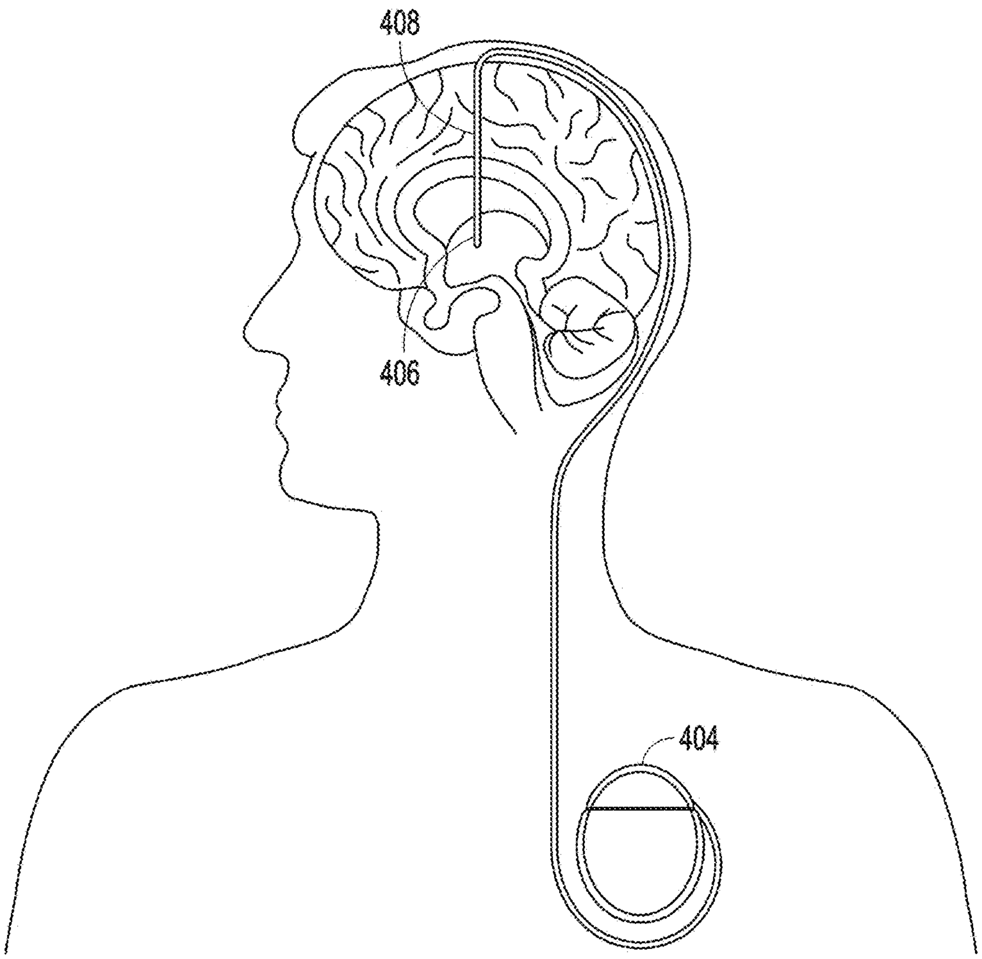
FIG. 4 is an illustration of another example of an IPG and an implantable lead system.

FIG. 4 illustrates another example of an IPG 404 and an implantable lead system 408 arranged to provide neurostimulation to a patient. An example of IPG 404 includes IPG 14 of FIGS. 2 and 3. An example of lead system 408 includes one or more of leads 12A and 12B in FIG. 3. The distal end 406 of the lead includes multiple electrodes (e.g., electrodes 26 in FIG. 3). In the illustrated embodiment, implantable lead system 408 is arranged to provide Deep Brain Stimulation (DBS) to a patient, with the stimulation target being neuronal tissue in a subdivision of the thalamus of the patient's brain. Other examples of DBS targets include neuronal tissue of the globus pallidus (GPi), the subthalamic nucleus (STN), the pedunculopontine nucleus (PPN), substantia nigra pars reticulate (SNr), cortex, globus pallidus externus (GPe), medial forebrain bundle (MFB), periaquaductal gray (PAG), periventricular gray (PVG), habenula, subgenual cingulate, ventral intermediate nucleus (VIM), anterior nucleus (AN), other nuclei of the thalamus, zona incerta, ventral capsule, ventral striatum, nucleus accumbens, and any white matter tracts connecting these and other structures.

After implantation, a clinician will program the neurostimulation device 400 using a CP 18, remote control, or other programming device. The programmed neurostimulation device 400 can be used to treat a neurological condition of the patient, such as Parkinson's Disease, Tremor, Epilepsia, Alzheimer's Disease, other Dementias, Stroke, Multiple Sclerosis, Amyotrophic Lateral Sclerosis (ALS), Autism, brain injury, brain tumor, migraine or other pain or headache condition, and any neurological syndromes that are congenic, degenerative, or acquired.

Returning to FIG. 3, the electronic circuitry of IPG 14 can include a stimulation control circuit that controls delivery of the neurostimulation energy. The stimulation control circuit can include a microprocessor, a digital signal processor, application specific integrated circuit (ASIC), or other type of processor, interpreting or executing instructions included in software or firmware. The neurostimulation energy can be delivered according to specified (e.g., programmed) modulation parameters. Examples of setting modulation parameters can include, among other things, selecting the electrodes or electrode combinations used in the stimulation, configuring an electrode or electrodes as the anode or the cathode for the stimulation, specifying the percentage of the neurostimulation provided by an electrode or electrode combination, and specifying stimulation pulse parameters. Examples of pulse parameters include, among other things, the amplitude of a pulse (specified in current or voltage), pulse duration (e.g., in microseconds), pulse rate (e.g., in pulses per second), and parameters associated with a pulse train or pattern such as burst rate (e.g., an "on" modulation time followed by an "off" modulation time), amplitudes of pulses in the pulse train, polarity of the pulses, etc.

Figure 5:
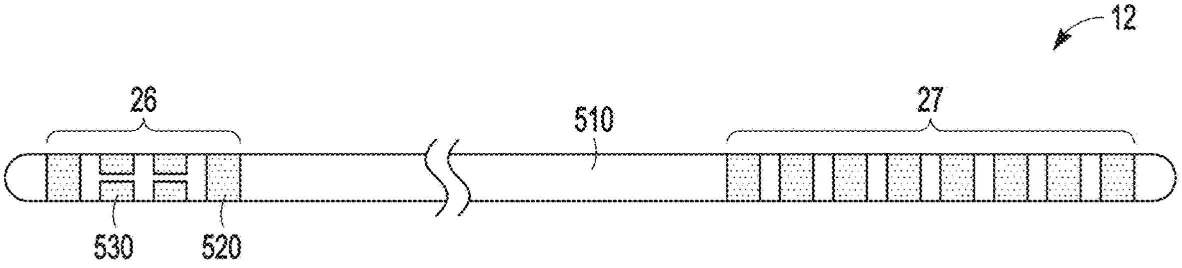
FIG. 5 is a schematic side view of an example of an electrical stimulation lead.

FIG. 5 is a schematic side view of an embodiment of an electrical stimulation lead. FIG. 5 illustrates a stimulation lead 12 with electrodes 26 disposed at least partially about a circumference of the lead 12 along a distal end portion of the lead and terminals 27 disposed along a proximal end portion of the lead. The lead 12 can be implanted near or within the desired portion of the body to be stimulated (e.g., the brain, spinal cord, or other body organs or tissues). In one example of operation for deep brain stimulation, access to the desired position in the brain can be accomplished by drilling a hole in the patient's skull or cranium with a cranial drill (commonly referred to as a burr), and coagulating and incising the dura mater, or brain covering. The lead 12 can be inserted into the cranium and brain tissue with the assistance of a stylet (not shown). The lead 12 can be guided to the target location within the brain using, for example, a stereotactic frame and a microdrive motor system. In some embodiments, the microdrive motor system can be fully or partially automatic. The microdrive motor system may be configured to perform one or more the following actions (alone or in combination): insert the lead 12, advance the lead 12, retract the lead 12, or rotate the lead 12.

In some embodiments, measurement devices coupled to the muscles or other tissues stimulated by the target neurons, or a unit responsive to the patient or clinician, can be coupled to the implantable pulse generator or microdrive motor system. The measurement device, user, or clinician can indicate a response by the target muscles or other tissues to the stimulation or recording electrode(s) to further identify the target neurons and facilitate positioning of the stimulation electrode(s). For example, if the target neurons are directed to a muscle experiencing tremors, a measurement device can be used to observe the muscle and indicate changes in, for example, tremor frequency or amplitude in response to stimulation of neurons. Alternatively, the patient or clinician can observe the muscle and provide feedback.

The lead 12 for deep brain stimulation can include stimulation electrodes, recording electrodes, or both. In at least some embodiments, the lead 12 is rotatable so that the stimulation electrodes can be aligned with the target neurons after the neurons have been located using the recording electrodes. Stimulation electrodes may be disposed on the circumference of the lead 12 to stimulate the target neurons. Stimulation electrodes may be ring-shaped so that current projects from each electrode equally in every direction from the position of the electrode along a length of the lead 12. In the embodiment of FIG. 5, two of the electrodes 520 are ring electrodes 520. Ring electrodes typically do not enable stimulus current to be directed from only a limited angular range around of the lead. Segmented electrodes 530, however, can be used to direct stimulus current to a selected angular range around the lead. When segmented electrodes 530 are used in conjunction with an IPG 14 that delivers constant current stimulus, current steering can be achieved to more precisely deliver the stimulus to a position around an axis of the lead (e.g., radial positioning around the axis of the lead). To achieve current steering, segmented electrodes can be utilized in addition to, or as an alternative to, ring electrodes.

The lead 12 includes a lead body 510, terminals 27, and one or more ring electrodes 520 and one or more sets of segmented electrodes 530 (or any other combination of electrodes). The lead body 510 can be formed of a biocompatible, non-conducting material such as, for example, a polymeric material. Suitable polymeric materials include, but are not limited to, silicone, polyurethane, polyurea, polyurethaneurea, polyethylene, or the like. Once implanted in the body, the lead 12 may be in contact with body tissue for extended periods of time. In at least some embodiments, the lead 12 has a cross-sectional diameter of no more than 1.5 millimeters (1.5 mm) and may be in the range of 0.5 to 1.5 mm. In at least some embodiments, the lead 12 has a length of at least 10 centimeters (10 cm) and the length of the lead 12 may be in the range of 10 to 70 cm.

The electrodes 26 can be made using a metal, alloy, conductive oxide, or any other suitable conductive biocompatible material. Examples of suitable materials include, but are not limited to, platinum, platinum iridium alloy, iridium, titanium, tungsten, palladium, palladium rhodium, or the like. Preferably, the electrodes are made of a material that is biocompatible and does not substantially corrode under expected operating conditions in the operating environment for the expected duration of use. Each of the electrodes can either be used or unused (OFF). When the electrode is used, the electrode can be used as an anode or cathode and carry anodic or cathodic current. In some instances, an electrode might be an anode for a period of time and a cathode for a period of time.

Deep brain stimulation leads and other leads may include one or more sets of segmented electrodes. Segmented electrodes may provide for superior current steering than ring electrodes because target structures in deep brain stimulation or other stimulation are not typically symmetric about the axis of the distal electrode array. Instead, a target may be located on one side of a plane running through the axis of the lead. Through the use of a radially segmented electrode array ("RSEA"), current steering can be performed not only along a length of the lead but also around a circumference of the lead. This provides precise three-dimensional targeting and delivery of the current stimulus to neural target tissue, while potentially avoiding stimulation of other tissue.

Any number of segmented electrodes 530 may be disposed on the lead body 510 including, for example, anywhere from one to sixteen or more segmented electrodes 530. It will be understood that any number of segmented electrodes 530 may be disposed along the length of the lead body 510. A segmented electrode 530 typically extends only 75%, 67%, 60%, 50%, 40%, 33%, 25%, 20%, 17%, 15%, or less around the circumference of the lead.

The segmented electrodes 530 may be grouped into sets of segmented electrodes, where each set is disposed around a circumference of the lead 12 at a particular longitudinal portion of the lead 12. The lead 12 may have any number segmented electrodes 530 in a given set of segmented electrodes. The lead 12 may have one, two, three, four, five, six, seven, eight, or more segmented electrodes 530 in a given set. In at least some embodiments, each set of segmented electrodes 530 of the lead 12 contains the same number of segmented electrodes 530. The segmented electrodes 530 disposed on the lead 12 may include a different number of electrodes than at least one other set of segmented electrodes 530 disposed on the lead 12. The segmented electrodes 530 may vary in size and shape. In some embodiments, the segmented electrodes 530 are all of the same size, shape, diameter, width or area or any combination thereof. In some embodiments, the segmented electrodes 530 of each circumferential set (or even all segmented electrodes disposed on the lead 12) may be identical in size and shape.

Each set of segmented electrodes 530 may be disposed around the circumference of the lead body 510 to form a substantially cylindrical shape around the lead body 510. The spacing between individual electrodes of a given set of the segmented electrodes may be the same, or different from, the spacing between individual electrodes of another set of segmented electrodes on the lead 12. In at least some embodiments, equal spaces, gaps or cutouts are disposed between each segmented electrode 530 around the circumference of the lead body 510. In other embodiments, the spaces, gaps or cutouts between the segmented electrodes 530 may differ in size, or cutouts between segmented electrodes 530 may be uniform for a particular set of the segmented electrodes 530 or for all sets of the segmented electrodes 530. The sets of segmented electrodes 530 may be positioned in irregular or regular intervals along a length the lead body 510.

Conductor wires (not shown) that attach to the ring electrodes 520 or segmented electrodes 530 extend along the lead body 510. These conductor wires may extend through the material of the lead 12 or along one or more lumens defined by the lead 12, or both. The conductor wires couple the electrodes 520, 530 to the terminals 27.

Figure 6A:
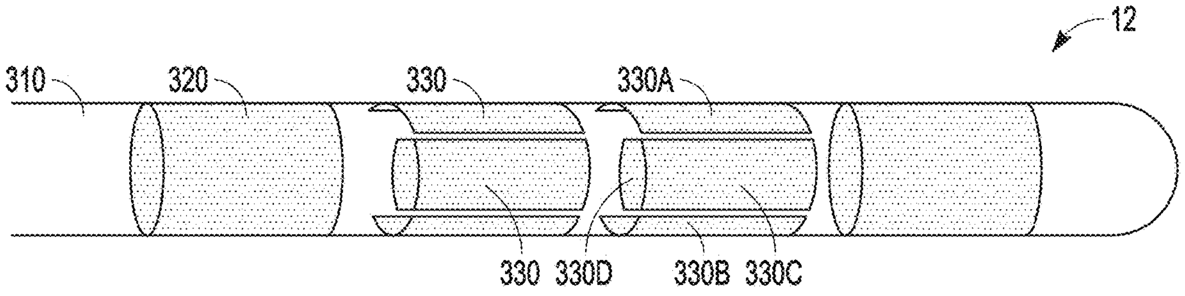
FIGS. 6A-6H are illustrations of an example of electrodes of a stimulation lead.
Figure 6B:
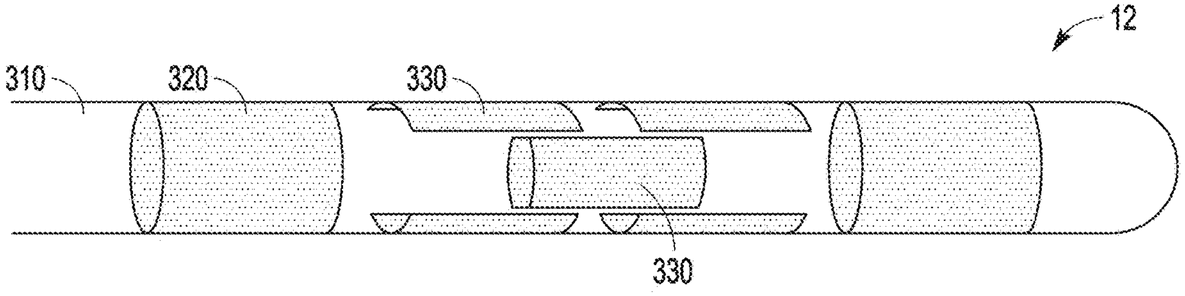
Figure 6C:
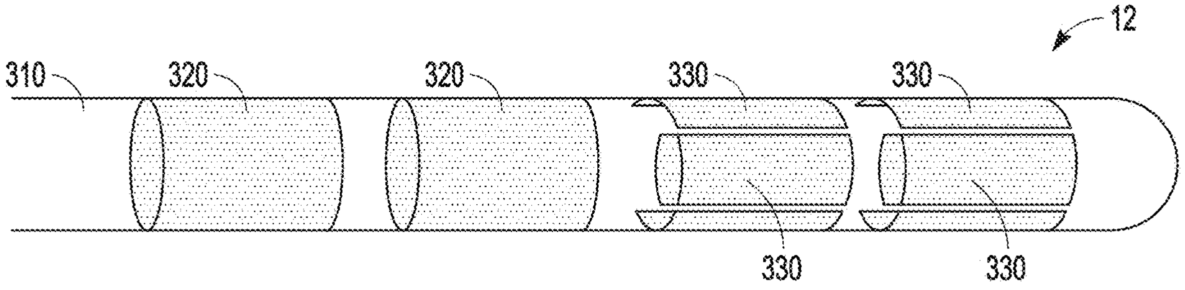
Figure 6D:
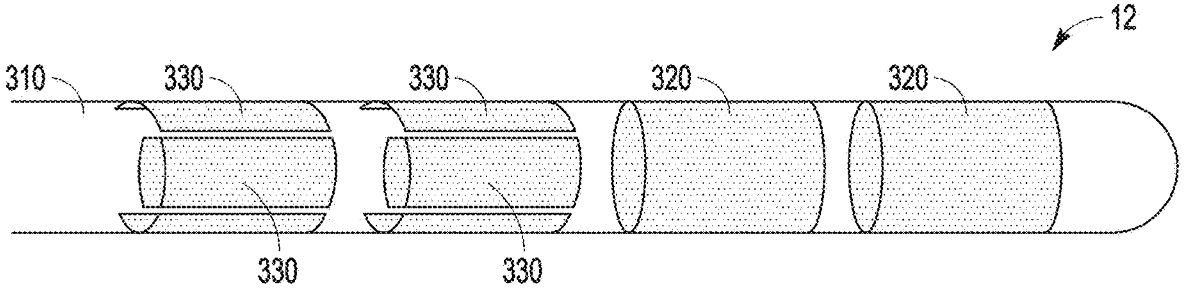
Figure 6E:
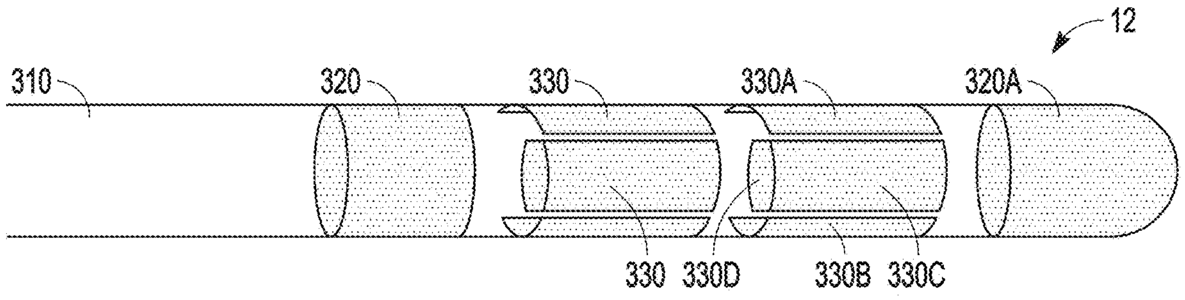
Figure 6F:
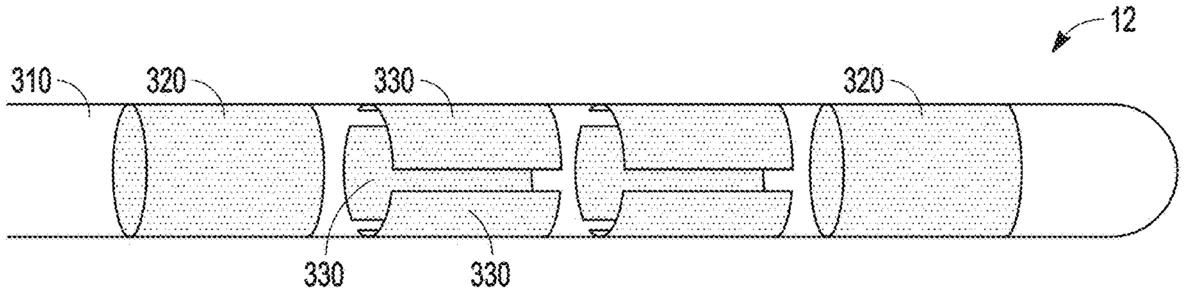
Figure 6G:
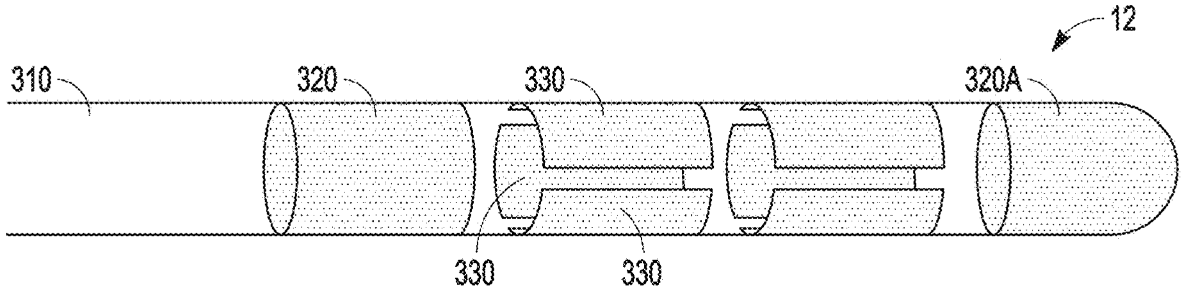
Figure 6H:
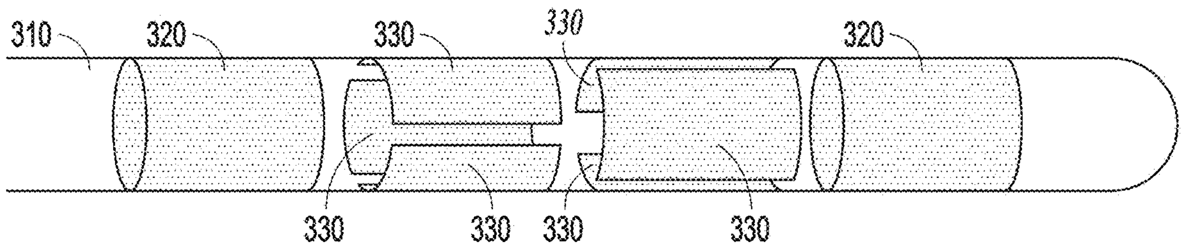

FIGS. 6A-6H are illustrations of different embodiments of leads 12 with segmented electrodes 330, optional ring electrodes 320 or tip electrodes 320*a*, and a lead body 310. The sets of segmented electrodes 330 each include either two (FIG. 6B), three (FIGS. 6E-6H), or four (FIGS. 6A, 6C, and 6D) or any other number of segmented electrodes including, for example, three, five, six, or more. The sets of segmented electrodes 330 can be aligned with each other (FIGS. 6A-6G) or staggered (FIG. 6H).

When the lead 12 includes both ring electrodes 320 and segmented electrodes 330, the ring electrodes 320 and the segmented electrodes 330 may be arranged in any suitable configuration. For example, when the lead 12 includes two ring electrodes 320 and two sets of segmented electrodes 330, the ring electrodes 120 can flank the two sets of segmented electrodes 330 (see e.g., FIGS. 5, 6A, and 6E-6H, ring electrodes 320 and segmented electrode 330). Alternately, the two sets of ring electrodes 320 can be disposed proximal to the two sets of segmented electrodes 330 (see e.g., FIG. 6C, ring electrodes 320 and segmented electrode 330), or the two sets of ring electrodes 320 can be disposed distal to the two sets of segmented electrodes 330 (see e.g., FIG. 6D, ring electrodes 320 and segmented electrode 330). One of the ring electrodes can be a tip electrode (see e.g., tip electrode 320*a* of FIGS. 36E and 6G). It will be understood that other configurations are possible as well (e.g., alternating ring and segmented electrodes, or the like).

By varying the location of the segmented electrodes 330, different coverage of the target neurons may be selected. For example, the electrode arrangement of FIG. 6C may be useful if the physician anticipates that the neural target will be closer to a distal tip of the lead body 310, while the electrode arrangement of FIG. 6D may be useful if the physician anticipates that the neural target will be closer to a proximal end of the lead body 310.

Any combination of ring electrodes 320 and segmented electrodes 330 may be disposed on the lead 12. For example, the lead 12 may include a first ring electrode 320, two sets of segmented electrodes; each set formed of four segmented electrodes 330, and a final ring electrode 320 at the end of the lead. This configuration may simply be referred to as a 1-4-4-1 configuration (FIGS. 6A and 6E, ring electrodes 320 and segmented electrode 330). It may be useful to refer to the electrodes with this shorthand notation. Thus, the embodiment of FIG. 6C may be referred to as a 1-1-4-4 configuration, while the embodiment of FIG. 6D may be referred to as a 4-4-1-1 configuration. The embodiments of FIGS. 6F, 6G, and 6H can be referred to as a 1-3-3-1 configuration. Other electrode configurations include, for example, a 2-2-2-2 configuration, where four sets of segmented electrodes are disposed on the lead, and a 4-4 configuration, where two sets of segmented electrodes, each having four segmented electrodes 330 are disposed on the lead. The 1-3-3-1 electrode configuration of FIGS. 6F, 6G, and 6H has two sets of segmented electrodes, each set containing three electrodes disposed around the circumference of the lead, flanked by two ring electrodes (FIGS. 6F and 6H) or a ring electrode and a tip electrode (FIG. 6G). In some embodiments, the lead includes 16 electrodes. Possible configurations for a 16-electrode lead include but are not limited to 4-4-4-4; 8-8; 3-3-3-3-3-1 (and all rearrangements of this configuration); and 2-2-2-2-2-2-2-2.

Any other suitable arrangements of segmented and/or ring electrodes can be used. As an example, arrangements in which segmented electrodes are arranged helically with respect to each other. One embodiment includes a double helix. One or more electrical stimulation leads can be implanted in the body of a patient (for example, in the brain or spinal cord of the patient) and used to stimulate surrounding tissue. The lead(s) are coupled to the implantable pulse generator (such as IPG 14 in FIG. 2).

Figure 7:
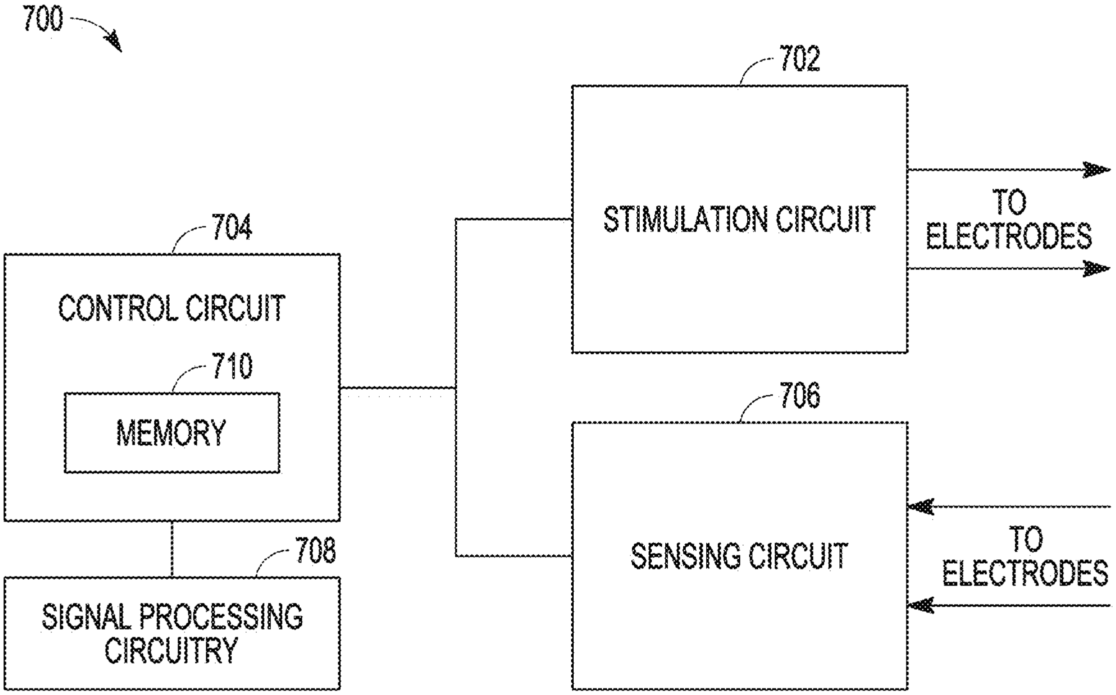
FIG. 7 is a block diagram of portions of an example of a medical device for providing neurostimulation.

FIG. 7 is a block diagram of portions of an embodiment of a neurostimulation system 700 for providing neurostimulation. The neurostimulation system 700 includes a stimulation circuit 702, a control circuit 704, and a sensing circuit 706. The stimulation circuit 702 can be operatively coupled to stimulation electrodes such as any of the electrodes described herein and the stimulation circuit 702 provides or delivers electrical neurostimulation energy to the electrodes. The control circuit 704 can include a processor such as a microprocessor, a digital signal processor, application specific integrated circuit (ASIC), or other type of processor, interpreting or executing instructions in software modules or firmware modules. The instructions can be stored in memory 710 that can be integral to the control circuit 704 or separate from the control circuit 704. The control circuit 704 can include other circuits or sub-circuits to perform the functions described. These circuits may include software, hardware, firmware, or any combination thereof. Multiple functions can be performed in one or more of the circuits or subcircuits as desired.

The neurostimulation system 700 includes a sensing circuit 706. An example of the sensing circuit 706 includes one or more sense amplifiers switchable among recording electrodes to sense internal neural signals of the patient. The neurostimulation system 700 includes signal processing circuitry 708. The signal processing circuitry 708 can include one or more processes running on a processor to perform signal analysis or other signal processing on the neural signals sensed using the sensing circuit 706.

The neurostimulation system 700 is connectable to at least one stimulation lead (e.g., stimulation lead 12 in FIG. 5) that can be implanted in the body of a patient (for example, in the brain of the patient) and the electrodes of the stimulation lead is used to stimulate surrounding tissue. The neurostimulation system 700 can sense electrical neural signals when coupled to electrodes implanted in the brain. The neurostimulation system 700 can be used at the time of implanting or sometime after implant to sense the response of the patient to neurostimulation. The sensed response can be used to adjust the neurostimulation by either an automatic adjustment of the parameters of the neurostimulation or by recommending parameter settings to a user.

The neurostimulation system can be included in one device or in multiple devices. For example, the stimulation circuit 702, sensing circuit 706, control circuit 704, and signal processing circuitry 708 can be included in an external neurostimulator (e.g., ETS 20 in FIG. 2) or in an internal neurostimulator (e.g., IPG 14 in FIG. 2). In some examples, the stimulation circuit 702, sensing circuit 706, and control circuit 704 can be included in an IPG and the signal processing circuitry 708 can be included in an IPG programming device (e.g., CP 18 in FIG. 2).

The human nervous system produces a neural response to neurostimulation received via sensory receptors or received directly into any part of the network of neural elements that forms the nervous system. Additionally, neurostimulation can excite elements of the human nervous system in a manner that produces neural responses. These neural responses are known as evoked potentials and the stimulation that evokes these responses can be called evoking neurostimulation. Evoked potential (EP) signals can be sensed electrically by the neurostimulation system 700, such as by using sense amplifiers of the sensing circuit 706 coupled to recording electrodes for example. A single or repetitive stimulus can be applied or presented to the nervous system and the evoked potential signals (e.g., evoked resonant neural activity (ERNA) signals) sensed from the presentations can be processed (e.g., filtered by averaging) to detect presence of evoked potentials.

The signal processing circuitry 708 can determine whether the sensed electrical signals are evoked potential signals (e.g., evoked resonant neural activity (ERNA) signals, DBS local evoked Potential (DLEP) signals, etc.) or noise or other signal artifact. Correct system or device-based detecting and classifying evoked potential signals distinguishes useful neural signal information from non-useful neural signal information. Device-based analysis on correctly classified evoked potential signals can improve conclusions reached by neurostimulation devices regarding neurostimulation therapy.

Figure 8:
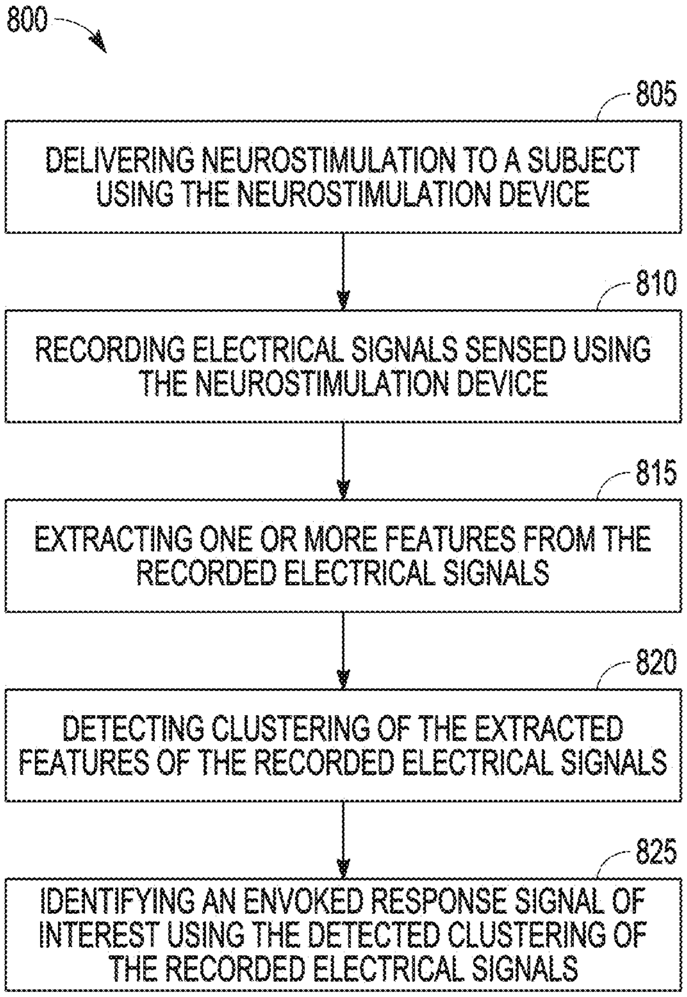
FIG. 8 is a flow diagram of a method to operate a neurostimulation system.

FIG. 8 is a flow diagram of an example of operating a neurostimulation device or system to deliver electrical neurostimulation. The device includes a stimulation circuit (e.g., stimulation circuit 702 in FIG. 7) operatively coupled to a stimulation lead (e.g., stimulation lead 12 in FIG. 2) that is implantable in a patient or subject. The stimulation lead can include multiple electrodes, including one or both of ring electrode and segmented electrodes.

Figure 9:
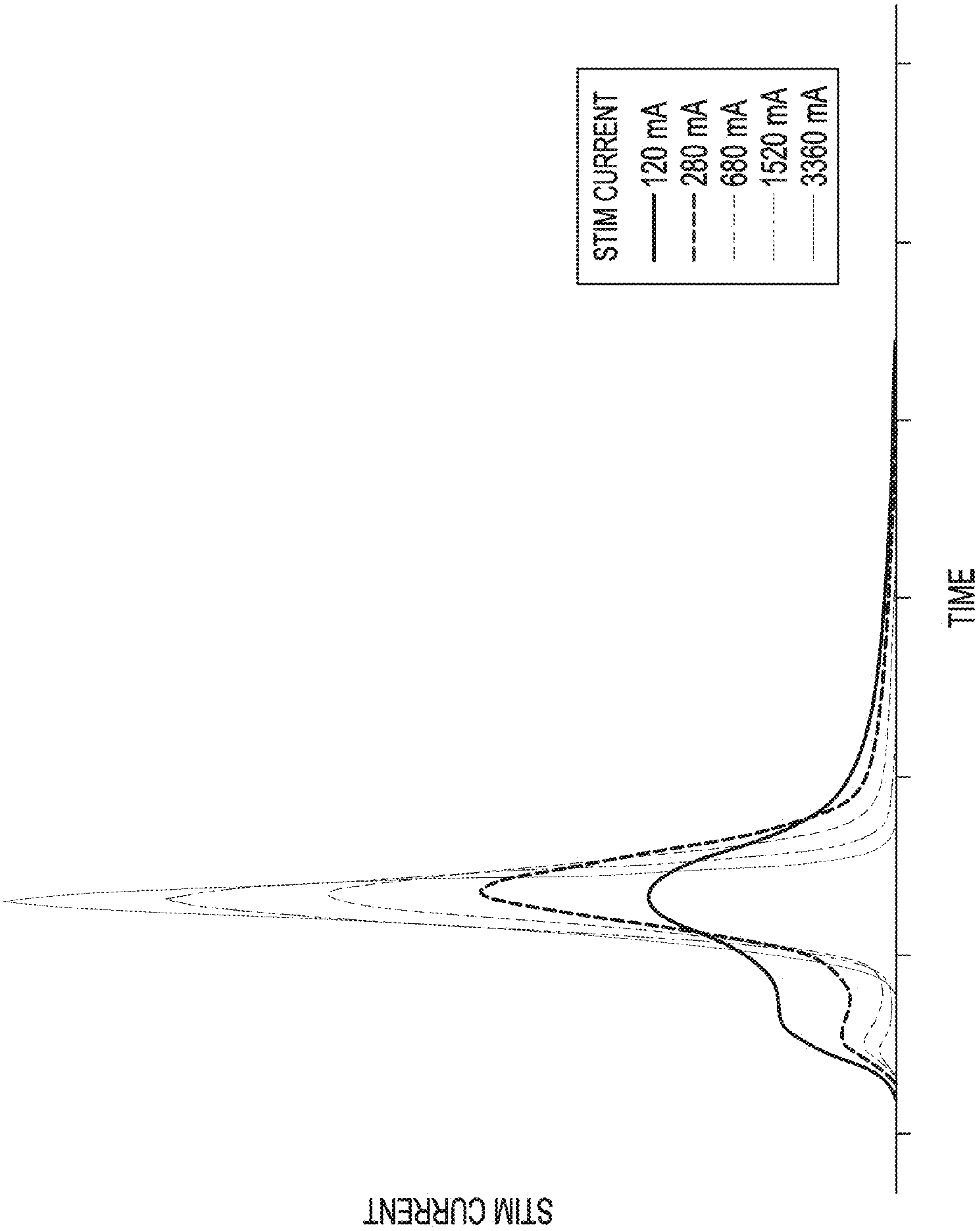
FIG. 9 is a graph of an example of a sweep of neurostimulation energy.

At block 805, evoking neurostimulation energy is delivered to the patient or subject using the neurostimulation device. The timing of the neurostimulation delivery can be controlled using a control circuit of the neurostimulation device (e.g., control circuit 704 of FIG. 7). In some examples, the control circuit sweeps location of the neurostimulation by sweeping the delivery of the neurostimulation among the electrodes and electrode segments of the stimulation lead. In some examples, the control circuit sweeps a stimulation parameter of (e.g., stimulation current amplitude) during delivery of the neurostimulation. FIG. 9 is a graph of an example of a sweep of stimulation current sweep. The stimulation current can be applied to the electrodes and segmented electrodes of a neurostimulation lead.

At block 810, electrical signals are sensed and recorded using the neurostimulation device. The electrical signals are sensed using a signal sensing circuit (e.g., sensing circuit 706 in FIG. 2). The sensed electrical signals are recorded such as by sampling the sensed electrical signals and storing the sensed electrical signals in the memory of the neurostimulation device (e.g., memory 710 in FIG. 2). The recorded signals may be the signals resulting from one or more sweeps performed by the neurostimulation device. The recorded electrical signals may include evoked response signals (e.g., ERNA signals and DLEP signals) and signal artifacts (e.g., noise signals).

It is desirable for the neurostimulation device to distinguish the evoked response signals of interest from other signals or signal artifacts. The evoked response signals of interest can be used by the neurostimulation device to score, recommend, or determine appropriate stimulation parameters (e.g., the set of electrodes used to deliver current, the polarity and relative strength of same, the magnitude, the amplitude, pulse-width, rate, or pattern of stimulation, etc.) to customize neurostimulation for the patient (including, updating or adjusting stimulation parameters, including intermittently or continuously, including when the initialization or update is done with a programming person or in an semi or fully automated or autonomous fashion), or to provide recommendations regarding lead positioning for the neurostimulation. If undesired signals or signal artifacts are incorrectly interpreted as the evoked response signals of interest, the neurostimulation or lead positioning derived by the neurostimulation device may be less effective.

To distinguish evoked response signals from signal artifacts, the similarity of the recorded electrical signals may be assessed by the device, and the recorded electrical signals that are most similar to each other are identified as evoked response signals, and the recorded electrical signals that are most dissimilar to the other recorded signals (e.g., outlier signals) are designated as signal artifacts. One approach to assessing the similarity of the recorded electrical signals is for the device to detect clustering in the recorded electrical signals.

At block 815, features of the recorded electrical signals are extracted (e.g., by using signal processing circuitry 708 in FIG. 7). Examples of the signal features include the greatest value of the magnitude of the signals, the amplitude of a detected peak in the signals (e.g., first negative peak, first positive peak, or other peak in the signals), the time of the detected peak, phase of the signals, frequency of the signals, etc. Other features, combinations of features, and sets of features could equivalently be used. At block 820, the neurostimulation device detects clustering of the one or more extracted features of the recorded electrical signals. And at block 825, the detected clustering is presented (e.g., displayed) to a user. The clustering of the signal features can be used by the neurostimulation device to identify evoked response signals of interest in the recorded electrical signals.

Figure 10A:
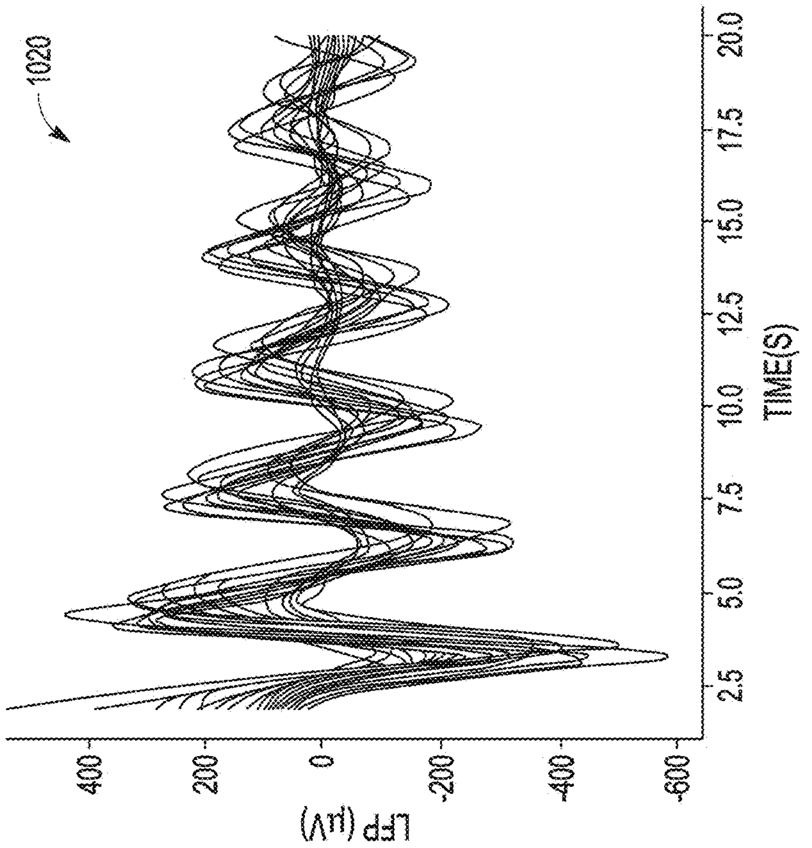
FIGS. 10A-10C illustrate examples of electrical signals that may be sampled, recorded, and processed by a neurostimulation device.
Figure 10B:
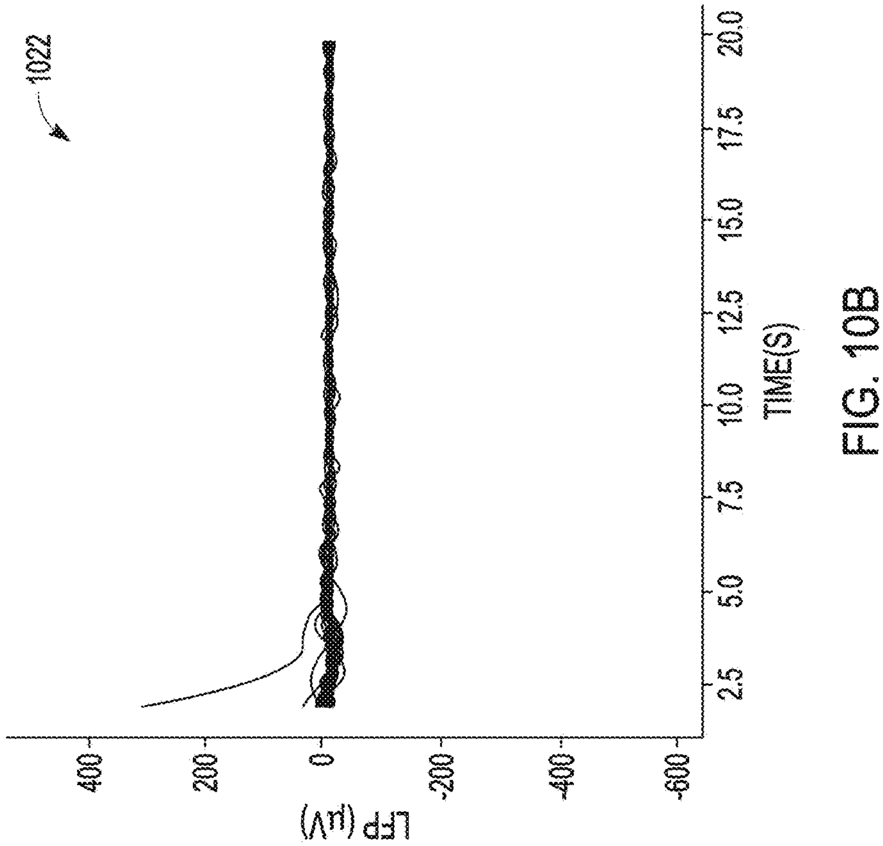
Figure 10C:
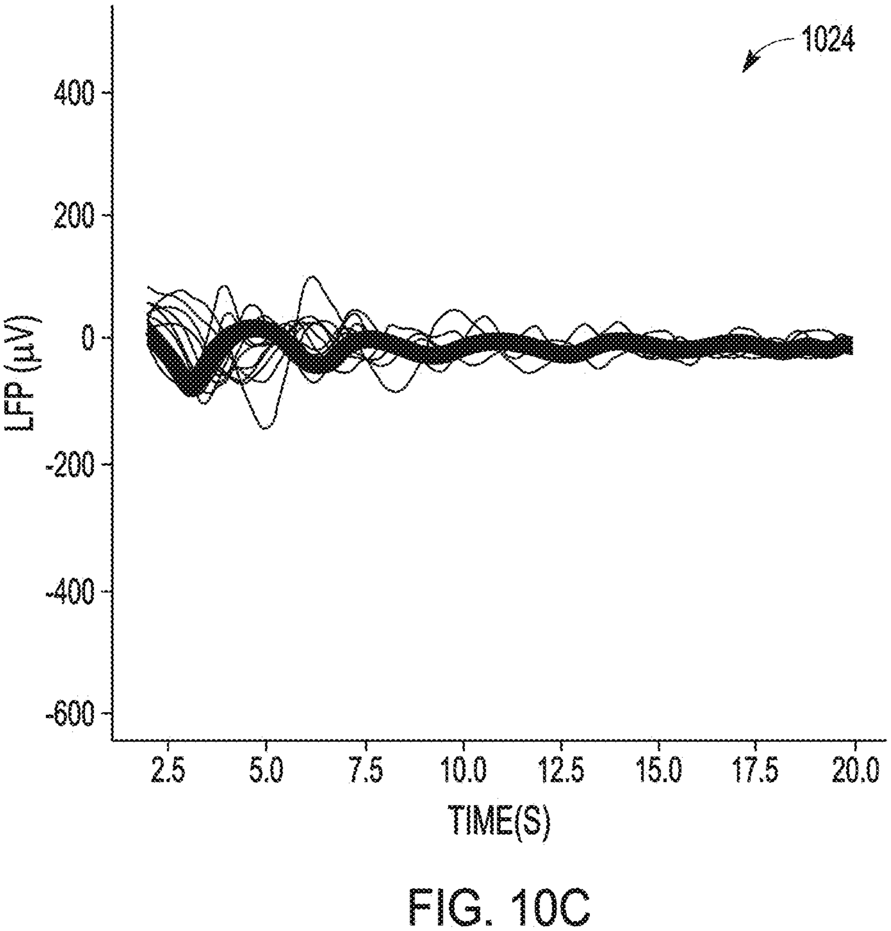
Figure 11:
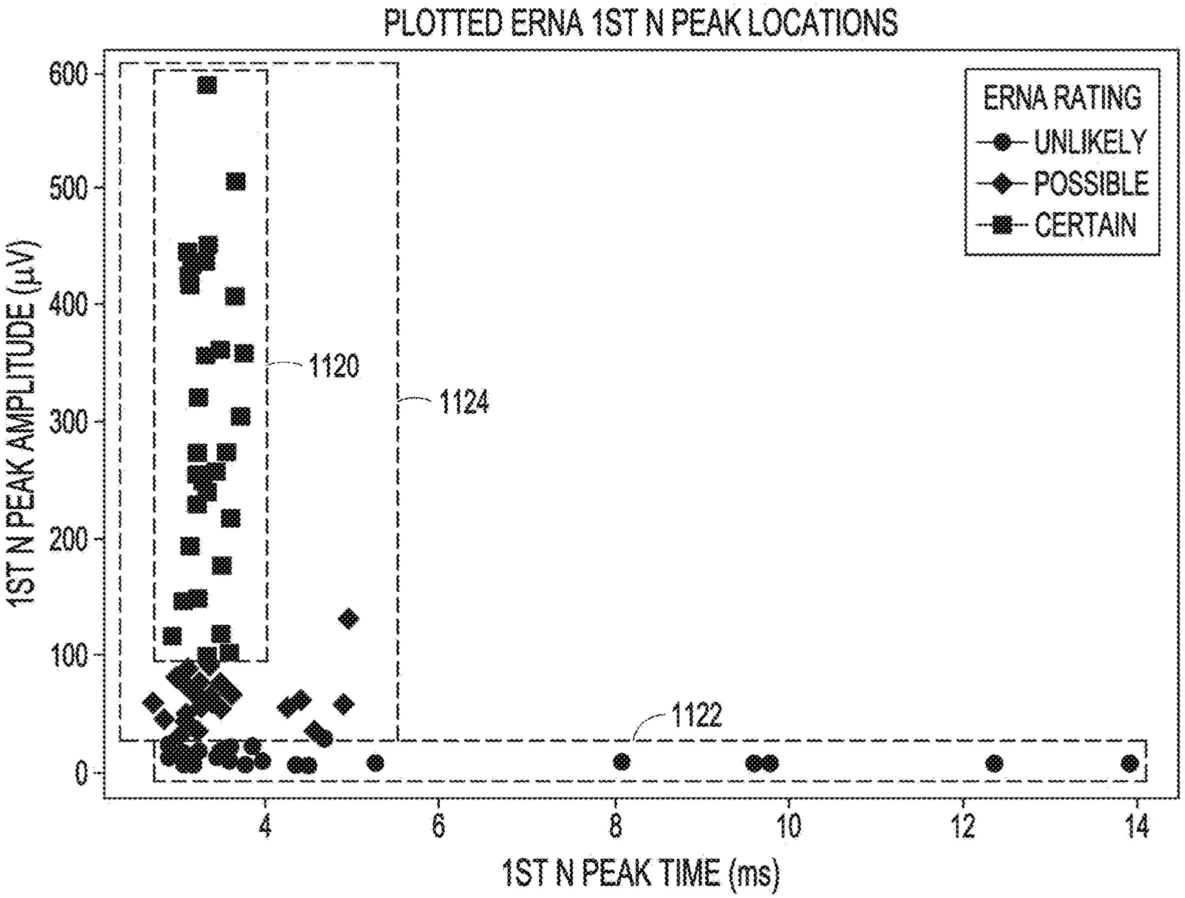
FIG. 11 is an example of a plot of the amplitudes of the first negative peak of the signals in FIG. 10.

FIGS. 10A-10C illustrate examples of electrical signals sampled and recorded by the neurostimulation device that may include evoked response signals and signal artifacts. The electrical signals may be processed by the signal processing circuitry 708 such as by filtering and amplification. FIG. 11 is a plot of the amplitudes of the first negative peak (1st N peak) of the signals in FIGS. 10A-10C and the time of occurrence of the first negative peak. The points of the plot grouped in the dashed-line box 1120 correspond to the first negative peaks of the ERNA signals 1020 in FIG. 10A. The points can be selected by the neurostimulation device as belonging to a signal cluster that a physician can be certain are true ERNA signals. The points grouped in the dashed-line box 1122 correspond to the first negative peaks of the ERNA signals 1022 in FIG. 10B. The first negative peaks in the dashed-line box 1122 are distant enough from the peaks in box 1120 that the signals in box 1122 can be designated by the neurostimulation device as signal artifacts and unlikely to be ERNA signals. The points of the plot outside the boxes 1120, 1122, correspond to the ERNA signals 1024 of FIG. 10C and may be designated as possible ERNA signals. The box 1124 can be drawn to classify the ERNA signals 1024 in FIG. 10C and the certain ERNA signals 1020 in FIG. 10A as the possible ERNA signals.

Various techniques can be used for clustering of the recorded electrical signals. For example, correlation among the recorded electrical signals could be calculated or otherwise determined, and the recorded signals that correlate the closest to each other could be designated as a signal cluster with the evoked response signals belonging to the cluster. In another example, a feature space could be derived for the recorded electrical signals (e.g., the amplitude and time feature space in the example of FIG. 11) and the distance between the signals in the feature space could be calculated. Those signals closest to each other in the feature space could be designated as a signal cluster with the evoked response signals belonging to the cluster. To determine which signals are closest to each other, the center of a candidate cluster can be determined (e.g., by determining a mean value for each dimension of the feature space) and a standard deviation could be found along each dimension. The signals with plots points within a standard deviation from the center can be included in the cluster.

Figure 12:
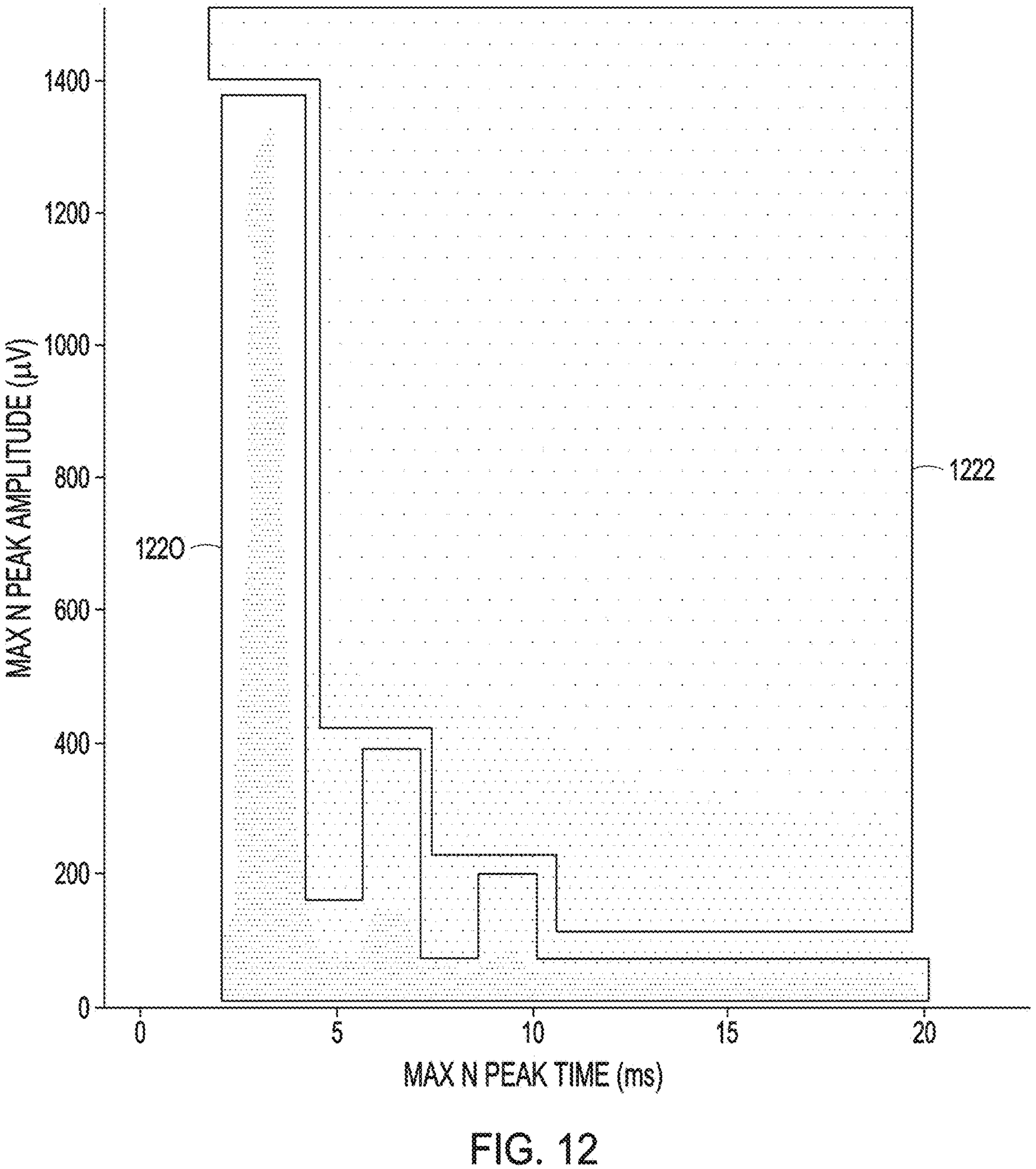
FIG. 12 is an example of a graph with the points of the graph corresponding to the maximum amplitude of a negative peak in recorded electrical signals.

The plot of FIG. 11 is a simplification for clarity of the example. FIG. 12 shows a more realistic graph with the points of the graph corresponding to the maximum amplitude of a negative peak (Max N Peak Amplitude) in the recorded electrical signals and the time of the maximum amplitude negative peak (Max N Peak Time). The graph may be presented to a user on a display of a user interface of the neurostimulation device or system. The points may be generated using one or more sweeps of stimulation amplitude across the electrodes of the stimulation lead. Each sweep may produce a set of evoked potential signals and a set of signal artifacts. The points of the graph may be generated from evoked response signal stored locally in the neurostimulation device or stored in a separate device with which the neurostimulation device can communicate information. The large number of points to be analyzed in the graph in the example of FIG. 12 shows the advantage of a device-based classification of the signals. The points within box 1220 of the graph are points belonging to detected clusters likely to correspond to evoked response signals and not to signal artifacts. The points within box 1222 of the graph are points likely to correspond to signal artifacts and not to evoked response signals. The points in the example of FIG. 12 includes two classifications of signals, but more than two classifications can be used.

Another example of a method of detecting clustering of the recorded electrical signals is to estimate the density of a feature space formed from the extracted features and compare the density of points in regions of the feature space to a density threshold. Regions may be designated as high density regions when the density of points in the region is greater than the threshold density. Recorded electrical signals in the high density region or regions of the feature space are classified as evoked response signals, and recorded electrical signals with features outside the high density regions are classified as signal artifacts.

Kernel density estimation (KDE) is one technique to estimate the density of the points in the feature space. The neurostimulation device determines values of a kernel function for the points of the feature space (e.g., the peak amplitude and peak time feature space of FIGS. 11 and 12). The KDE is determined from the kernel function for smoothing of the kernel function to estimate density of the feature space. In some examples, the neurostimulation device calculates the normalized log of the KDE. Using the normalized log of the KDE may improve sensitivity of the signal processing to lower values of the kernel function and improve the comparison of the values to a threshold across various numbers of recorded electrical signals. Regions determined to have a low density are assumed to contain only signals artifacts, and the identified signal artifacts are not included in any further analysis or decision-making by the neurostimulation device. A recorded electrical signal can be classified as an evoked response signal when the recorded electrical signal is included in the higher density region or regions.

Figure 13:
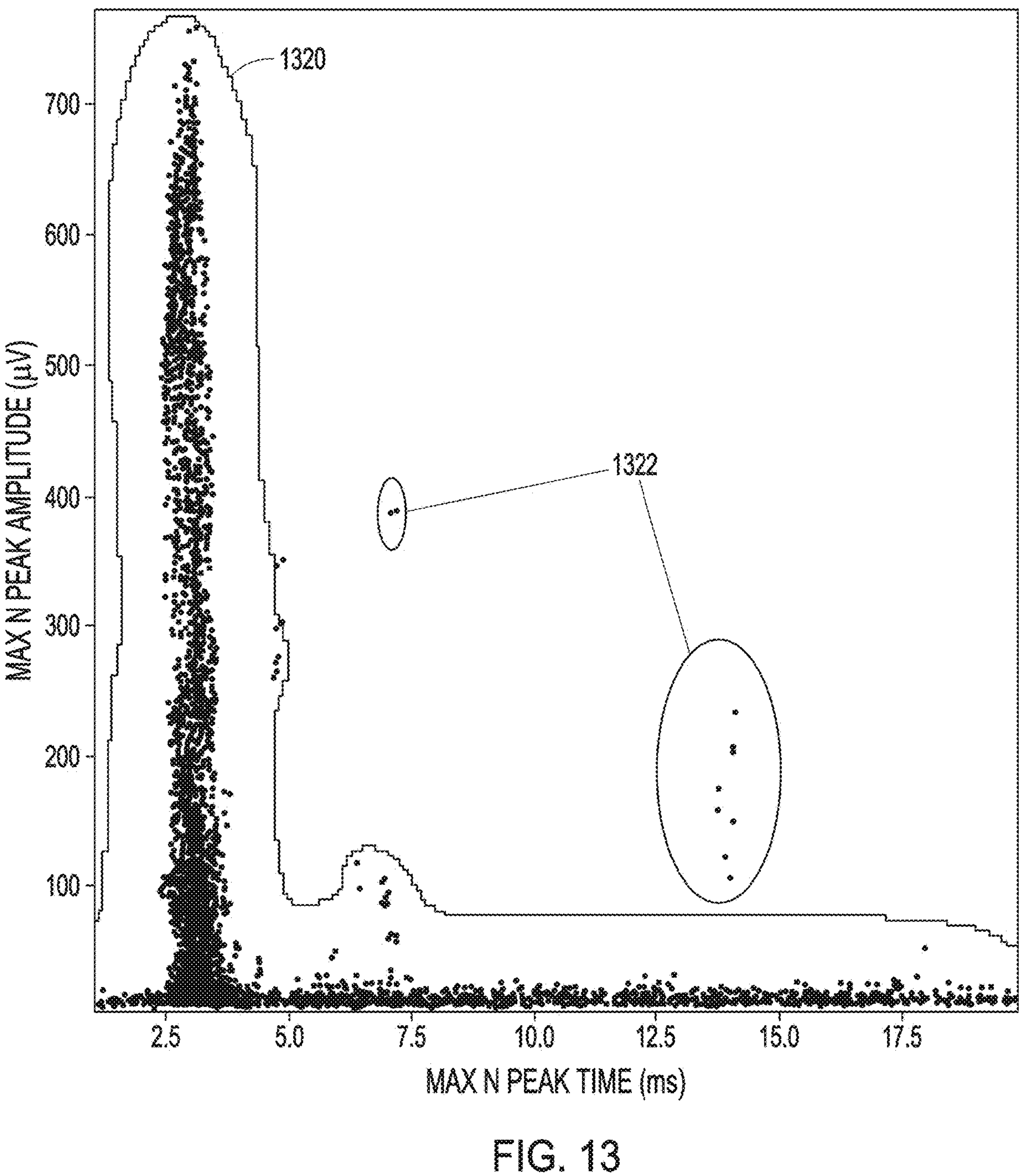
FIG. 13 is a plot of kernel density estimation (KDE) for recorded electrical signals.

FIG. 13 is a plot of the normalized log of the KDE for the maximum negative peak amplitude and the time of the maximum negative peak of recorded electrical signals. The line 1320 in the graph represents the boundary to a higher density region. The signals corresponding to the points within the boundary are identified as evoked response signals. The ovals 1322 are regions of low density. The signals corresponding to the points within the low density regions 1322 are classified as signal artifacts.

The identified evoked response signals are included in any further analysis, and the identified signal artifacts are excluded from the analysis. In some examples, the neurostimulation device produces a file of recorded electrical signals that only contains those recorded electrical signals classified as evoked response signals. The file of evoked response signals may be used for further analysis of the neurostimulation device or sent to a separate device. In some examples, only the recorded electrical signals classified as evoked response signals are displayed to a user. For instance, the clustering may result in identifying a set of evoked response signals that are highly likely to be ERNA signals, and only the identified evoked response signals highly likely to be ERNA signals are presented to a user in a display (e.g., such as ERNA signals 1020 in FIG. 10).

In some examples, the recorded electrical signals classified as evoked response signals are included in a training dataset that can be repeatedly fed into a machine learning model to refine the results of the model. The recorded electrical signals classified as signal artifacts are excluded from the training data set to improve the results of the model.

In some examples, the neurostimulation device adjusts the neurostimulation delivered to the patient using the one or more extracted features of recorded electrical signals identified as evoked response signals. For example, the neurostimulation device may identify multiple evoked response signals in the recorded electrical signals and set a stimulation configuration of the neurostimulation to the stimulation configuration that produced the highest amplitude evoked response signal of the identified multiple evoked response signals. The stimulation configuration may include a stimulation energy and an electrode combination that produced the highest amplitude evoked response signal. In some examples, the identified evoked response signals can be used to produce a recommendation regarding placement of the neurostimulation lead or lead electrodes to use for the stimulation. For instance, the neurostimulation device may recommend changing the lead position based on a flat response with a small amplitude due to a poor response in one or more identified evoked response signals.

The embodiments described herein can be methods that are machine or computer-implemented at least in part. Some embodiments may include a computer-readable medium or machine-readable medium encoded with instructions operable to configure an electronic device or system to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. Various embodiments are illustrated in the figures above. One or more features from one or more of these embodiments may be combined to form other embodiments.

The above detailed description is intended to be illustrative, and not restrictive. The scope of the disclosure should, therefore, be determined with references to the appended claims, along with the full scope of equivalents to which such claims are entitled.

What is claimed is:

1. A computer-implemented method of operating a neurostimulation device when connected to an implantable stimulation lead, the method comprising:

delivering neurostimulation to a subject using the neurostimulation device to evoke neural activity of the subject;

sensing, using the implantable stimulation lead, electrical signals resulting from the delivered neurostimulation;

recording the sensed electrical signals resulting from the delivered neurostimulation;

extracting one or more features from the recorded electrical signals;

detecting clustering of the one or more extracted features of the recorded electrical signals; and classifying, by the neurostimulation device, a recorded electrical signal of the recorded electrical signals as either an evoked response signal of interest or an artifact signal based on the detected clustering of the one or more extracted features of the recorded electrical signals and adjusting, by the neurostimulation device, the neurostimulation to the subject using the one or more extracted features of a classified evoked response signal of interest.

2. The method of claim 1, wherein the extracting the one or more features of the recorded electrical signals includes measuring a magnitude of the recorded electrical signals and a time of a greatest magnitude value of the recorded electrical signals;

wherein detecting clustering includes detecting a cluster of recorded electrical signals in a feature space including the greatest magnitude values and the times of the greatest magnitude values of the recorded electrical signals; and selecting the evoked response signal of interest from the detected cluster.

3. The method of claim 1, wherein the detecting the clustering includes classifying the recorded electrical signals as either the evoked response signal of interest signals or the artifact signal using kernel density estimation (KDE) of the one or more extracted features of the recorded electrical signals.

4. The method of claim 3, including:

determining a value of a kernel function for the recorded electrical signals using the one or more extracted features of the recorded electrical signals;

determining the KDE for the kernel function values;

identifying a higher density set of recorded electrical signals included in a region of the KDE having a density greater than a threshold density; and classifying a recorded electrical signal as the evoked response signal of interest when the recorded electrical signal is included in the higher density set of recorded electrical signals.

5. The method of claim 4, including:

calculating a normalized log of the KDE; and wherein the identifying the higher density set of recorded electrical signals includes identifying the higher density set of recorded electrical signals as the electrical signals included in a region of the normalized log of the KDE having a density greater than the threshold density.

6. The method of claim 3, including:

determining a value of a kernel function for the recorded electrical signals using the one or more extracted features of the recorded electrical signals;

determining the KDE for the kernel function values;

identifying a low density set of recorded electrical signals included in a region of the KDE having a density less than a threshold density; and classifying a candidate recorded electrical signal as the artifact signal when the candidate recorded electrical signal is included in the low density set of recorded electrical signals.

7. The method of claim 1, wherein the detecting the clustering includes determining correlation of the one or more extracted features among the recorded electrical signals.

8. The method of claim 1, wherein the detecting the clustering includes computing a distance between the recorded electrical signals in a feature space derived for the recorded electrical signals.

9. A neurostimulation device, the device comprising:

a stimulation circuit configured to deliver electrical neurostimulation to evoke neural activity of a subject when coupled to an implantable stimulation lead;

a sensing circuit configured to sense evoked neural activity signals resulting from the electrical neurostimulation when coupled to the stimulation lead;

a control circuit operatively coupled to the stimulation circuit and the sensing circuit, and configured to initiate delivery of neurostimulation to the subject and record sensed electrical signals resulting from the neurostimulation; and signal processing circuitry configured to:

extract one or more features from the recorded electrical signals;

detect clustering of the one or more extracted features of the recorded electrical signals; and classify a recorded electrical signal as either an evoked response signal of interest resulting from detected clustering, and adjust the neurostimulation to the subject using the one or more extracted features of a classified evoked response signal of interest.

10. The device of claim 9, wherein the signal processing circuitry is configured to identify a group of the recorded electrical signals as evoked response signals using kernel density estimation (KDE) of the one or more extracted features of the recorded electrical signals.

11. The device of claim 10, wherein the signal processing circuitry is configured to:

determine a value of a kernel function for the recorded electrical signals using the one or more extracted features of the recorded electrical signals;

determine the KDE for the kernel function values;

identify a higher density set of recorded electrical signals included in a region of the KDE having a density greater than a threshold density; and classify the recorded electrical signal as the evoked response signal of interest when the recorded electrical signal is included in the higher density set of recorded electrical signals.

12. The device of claim 11, wherein the signal processing circuitry is configured to:

calculate a normalized log of the KDE; and identify the higher density set of recorded electrical signals as the electrical signals included in a region of the normalized log of the KDE having a density greater than the threshold density.

13. The device of claim 9, wherein the signal processing circuitry is configured to:

determine a value of a kernel function for the recorded electrical signals using the one or more extracted features of the recorded electrical signals;

determine the KDE for the kernel function values;

identify a low density set of recorded electrical signals included in a region of the KDE having a density less than a threshold density; and classify a candidate recorded electrical signal as the artifact signal when the candidate recorded electrical signal is included in the low density set of recorded electrical signals.

14. The device of claim 9, wherein the signal processing circuitry is configured to detect the clustering of the one or more extracted features of the recorded electrical signals using correlation of the one or more extracted features among the recorded electrical signals.

15. The device of claim 9, wherein the signal processing circuitry is configured to:

derive a feature space for the one or more extracted features of the recorded electrical signals; and compute distance between the recorded electrical signals in the derived feature space.

16. The device of claim 9, wherein the signal processing circuitry is configured to:

measure a magnitude of the recorded electrical signals and a time of a greatest magnitude value of the recorded electrical signals;

determine a cluster of recorded electrical signals in a feature space including the greatest magnitude values and the times of the greatest magnitude values of the recorded electrical signals; and identify the evoked response signal of interest from the recorded electrical signals included in the determined cluster.

17. The device of claim 16, wherein the signal processing circuitry is configured to identify multiple evoked response signals of interest in the identified cluster of recorded electrical signals; and wherein the control circuit is configured to set a stimulation configuration of the neurostimulation to the stimulation configuration that produced the highest amplitude evoked response signal of the identified evoked response signals of interest.

18. A non-transitory computer readable storage medium including instructions that when performed by processing circuitry of a neurostimulation system, cause the neurostimulation system to perform actions including:

delivering neurostimulation energy to at least one implantable neurostimulation lead of the neurostimulation system to evoke neural activity of a subject;

recording electrical signals resulting from the neurostimulation that are sensed using the implantable neurostimulation lead;

extracting one or more features from the recorded electrical signals;

detecting clustering of the one or more extracted features of the recorded electrical signals;

classifying a recorded signal of the recorded electrical signals as either an evoked response activity signal or a signal artifact using the clustering of the one or more extracted features of the recorded electrical signals; and adjusting the neurostimulation based on the one or more extracted features of at least one identified evoked response signal.

19. The non-transitory computer readable storage medium of claim 18, further including instructions that when performed by the processing circuitry of the neurostimulation system, cause the neurostimulation system to perform actions including:

determining a value of a kernel function for the recorded electrical signals using the one or more extracted features of the recorded electrical signals;

determining a kernel density estimation (KDE) for the kernel function values;

identifying a higher density set of the recorded electrical signals included in a region of the KDE having a density greater than a threshold density, and identifying a lower density set of the recorded electrical signals included in a region of the KDE having a density lower than the threshold density; and classifying the recorded electrical signal as the evoked response activity signal when the recorded electrical signal is included in the higher density set of recorded electrical signals, and classifying the recorded electrical signal as the signal artifact when the recorded electrical signal is included in the lower density set of recorded electrical signals and, adjusting the neurostimulation to the subject using the one or more extracted features of a classified evoked response activity signal.

* * * * *